United States Patent [19]

Cabilly et al.

[11] Patent Number: 4,816,567

[45] Date of Patent: Mar. 28, 1989

[54] RECOMBINANT IMMUNOGLOBIN PREPARATIONS

[75] Inventors: Shmuel Cabilly, Monrovia; Herbert L. Heyneker, Burlingame; William E. Holmes, Pacifica; Arthur D. Riggs, La Verne; Ronald B. Wetzel, San Francisco, all of Calif.

[73] Assignee: Genentech, Inc., South San Francisco, Calif.

[21] Appl. No.: 483,457

[22] Filed: Apr. 8, 1983

[51] Int. Cl.$^4$ .................. C07K 15/14; C07K 15/06; C12P 21/00; C12N 15/00; C12N 1/20

[52] U.S. Cl. ........................... 530/387; 435/68; 435/172.3; 435/320; 435/252.3; 435/252.31; 435/252.33; 435/252.34; 435/10; 935/15; 935/29; 935/73; 530/388

[58] Field of Search ............ 435/68, 172.3, 240, 435/253, 172.2, 317, 320; 260/112 B; 536/27; 935/11, 15, 27, 29, 73; 530/387, 388

[56] References Cited

U.S. PATENT DOCUMENTS

| | | | |
|---|---|---|---|
| 4,444,878 | 4/1984 | Paulus | 435/188 |
| 4,512,922 | 4/1985 | Jones et al. | 435/68 X |
| 4,518,584 | 5/1985 | Mark et al. | 435/172.3 |
| 4,704,362 | 11/1987 | Itakura et al. | 435/172.3 X |

FOREIGN PATENT DOCUMENTS

| | | | |
|---|---|---|---|
| 0057107 | 8/1982 | European Pat. Off. | |
| 0073656 | 8/1982 | European Pat. Off. | 435/172.3 |
| 0068763 | 1/1983 | European Pat. Off. | |
| 0120694 | 10/1984 | European Pat. Off. | |

OTHER PUBLICATIONS

Dolby, T. W. et al. *Proc. Natl. Acad. Sci.*, vol. 77, (10) pp. 6027–6031, 1980.
Rice, D. et al. *Proc. Natl. Acad. Sci.* vol. 79 pp. 7862–7865, 1982.
Accolla, R. S. et al., *Proc. Natl. Acad. Sci.*, vol. 77, (1) pp. 563–566, 1980.
Raso, V. et al., *Cancer Res.*, vol. 41, pp. 2073–2078, 1981.
Nisonoff, A. et al., *Arch. Biochem. Biophys.*, vol. 93, pp. 460–462, 1960.
Glennie, M. J. et al., *Nature*, vol. 295, pp. 712–714, 1982.
Eisen, H. N., *Immunology*, Harper & Row, Publishers, pp. 415 and 428–436, 1974.
Hozumi, N. et al. *Nuc Acids Res.* vol. 5(6) pp. 1779–1799, Chem. Abst. 89:87928t, 1978.
Wetzel, R. et al. *Gene*, vol. 16, pp. 63–71, 1981.
Williams et al., *Science*, vol. 215, pp. 687–689, 1982.
Falkner, F. G. et al., Nature, vol. 298, pp. 286–288, 1982.
Boss et al. Hamer et al., Ed. "Gene Expressions-Proc. Cetus-UCLA Symposium . . . Mar. 26–Apr. 1, 1983" pp. 513–522.
Amster et al., "Nucleic Acid Research" 8(9): 2055–2065 (1980).
DeBoer et al., Rodriguez et al., Ed. "Promoters" 462–481 (1982).
Gough, "Tibs" 6(8): 203–205 (Aug. 1981).
Morrison, "J. of Immunology" 123(2): 793–800 (Aug. 1979).
Kohler "P.N.A.S. USA" 77(4): 2197–2199 (Apr. 1980).
Thomas M. Roberts, *Promoters*, Rodriguez et al., Eds. (1982), pp. 452–461.
Kemp et al., "Proc. Natl. Acad. Sci. USA" 78(7): 4520–4524 (Jul. 1981).
Valle et al., "Nature" 300:71–74 (4 Nov. 1982).
Microbiology 3rd ed., Harper Int. Ed. 338–379 (1980).
Hitzeman et al. Science 219: 620–625 (1983).
Mercereau-Puijalon et al., in "Expression of Eukaryotic Viral and Cellular Genes" Pettersson et al. (ED.) 295–303 (1981) Academic Pr.

*Primary Examiner*—Jayme Huleatt (List continued on next page.)

[57] ABSTRACT

Altered and native immunoglobulins, including constant-variable region chimeras, are prepared in recombinant cell culture. The immunoglobulins contain variable regions which are immunologically capable of binding predetermined antigens. Methods are provided for refolding directly expressed immunoglobulins into immunologically active form.

7 Claims, 15 Drawing Sheets

OTHER PUBLICATIONS

Keshet et al. Nucleic Acids Res. 9(1): 19–30 (1981).
Taniguchi et al., Proc. Natl. Acad. Sci. USA, 77(9): 5230–5233 (1980).
Ohsuye et al., Nucleic Acids Res. 11(5): 1283–1295 (1983).
Kadonaga et al., J. Biol. Chem. 259(4): 2149–2154 (1984).
Maniatis, T. "Molecular Cloning" p. 433 (Sep. 1985).
Fujisawa Y. et al. "Nucleic Acids Res." 11(11): 3581–3591 (1983).
Roberts, T. M. in "Promoters Structures and Function" Rodriguez, R. L. (ED.) 452–461 (1982).

RECOMBINANT IMMUNOGLOBIN PREPARATIONS

BACKGROUND OF THE INVENTION

This invention relates to the field of immunoglobulin production and to modification of naturally occuring immunoglobulin amino acid sequences. Specifically, the invention relates to using recombinant techniques to produce both immunoglobulins which are analogous to those normally found in vertebrate systems and to take advantage of these gene modification techniques to construct chimeric or other modified forms.

A. Immunoglobulins and Antibodies

Antibodies are specific immunoglobulin polypeptides produced by the vertebrate immune system in response to challenge by foreign proteins glycoproteins, cells, or other antigenic foreign substances. The sequence of events which permits the organism to overcome invasion by foreign cells or to rid the system of foreign substances is at least partially understood. An important part of this process is the manufacture of antibodies which bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicted it.

Immunoglobulins include both antibodies, as above described, and analogous protein substances which lack antigen specificity. The latter are produced at low levels by the lymph system and in increased levels by myelomas.

A.1 Source and Utility

Two major sources of vertebrate antibodies are presently utilized—generation in situ by the mammalian B lymphocytes and in cell culture by B-cell hybrids. Antibodies are made in situ as a result of the differentiation of immature B lymphocytes into plasma cells, which occurs in response to stimulation by specific antigens. In the undifferentiated B cell, the portions of DNA coding for the various regions on the immunoglobulin chains are separated in the genomic DNA. The sequences are reassembled sequentially prior to transcription. A review of this process has been given by Gough, *Trends in Biochem Sci*, 6: 203 (1981). The resulting rearranged genome is capable of expression in the mature B lymphocyte to produce the desired antibody. Even when only a single antigen is introduced into the sphere of the immune system for a particular mammal, however, a uniform population of antibodies does not result. The in situ immune response to any particular antigen is defined by the mosaic of responses to the various determinants which are present on the antigen. Each subset of homologous antibody is contributed by a single population of B cells—hence in situ generation of antibodies is "polyclonal".

This limited but inherent heterogeneity has been overcome in numerous particular cases by use of hybridoma technology to create "monoclonal" antibodies (Kohler, et al., *Eur. J. Immunol.*, 6: 511 (1976)). In this process, splenocytes or lymphocytes from a mammal which has been injected with antigen are fused with a tumor cell line, thus producing hybrid cells or "hybridomas" which are both immortal and capable of producing the genetically coded antibody of the B cell. The hybrids thus formed are segregated into single genetic strains by selection, dilution, and regrowth, and each strain thus represents a single genetic line. They therefore produce immunoreactive antibodies against a desired antigen which are assured to be homogenous, and which antibodies, referencing their pure genetic parentage, are called "monoclonal". Hybridoma technology has to this time been focused largely on the fusion of murine lines, but human-human hybridomas (Olsson, L. et al., *Proc. Natl. Acad. Sci. (USA)*, 77: 5429 (1980)); human-murine hybridomas (Schlom, J., et al. (ibid) 77: 6841 (1980)) and several other xenogenic hybrid combinations have been prepared as well. Alternatively, primary, antibody producing, B cells have been immortalized in vitro by transformation with viral DNA.

Polyclonal, or, much more preferably, monoclonal, antibodies have a variety of useful properties similar to those of the present invention. For example, they can be used as specific immunoprecipitating reagents to detect the presence of the antigen which elicited the initial processing of the B cell genome by coupling this antigen-antibody reaction with suitable detection techniques such as labeling with radioisotopes or with enzymes capable of assay (RIA, EMIT, and ELISA). Antibodies are thus the foundation of immuno diagnostic tests for many antigenic substances. In another important use, antibodies can be directly injected into subjects suffering from an attack by a substance or organism containing the antigen in question to combat this attack. This process is currently in its experimental stages, but its potential is clearly seen. Third, whole body diagnosis and treatment is made possible because injected antibodies are directed to specific target disease tissues, and thus can be used either to determine the presence of the disease by carrying with them a suitable label, or to attack the diseased tissue by carrying a suitable drug.

Monoclonal antibodies produced by hybridomas, while theoretically effective as suggested above and clearly preferable to polyclonal antibodies because of their specificity, suffer from certain disadvantages. First, they tend to be contaminated with other proteins and cellular materials of hybridoma, (and, therefore, mammalian) origin. Second, hybridoma lines producing monoclonal antibodies tend to be unstable and may alter the structure of antibody produced or stop producing antibody altogether (Kohler, G., et al., *Proc. Antl. Acad. Sci (USA)* 77: 2197 (1980); Morrison, S. L., *J. Immunol.* 123: 793 (1979)). The cell line genome appears to alter itself in response to stimuli whose nature is not currently known, and this alteration may result in production of incorrect sequences. Third, both hybridoma and B cells inevitably produce certain antibodies in glycosylated form (Melchers, F., *Biochemistry*, 10: 653 (1971)) which, under some circumstances, may be undesirable. Fourth, production of both monoclonal and polyclonal antibodies is relatively expensive. Fifth, and perhaps most important, production by current techniques (either by hybridoma or by B cell response) does not permit manipulation of the genome so as to produce antibodies with more effective design components than those normally elicited in response to antigens from the mature B cell in situ. The antibodies of the present invention do not suffer from the foregoing drawbacks, and, furthermore, offer the opportunity to provide molecules of superior design.

Even those immunoglobulins which lack the specificity of atibodies are useful, although over a smaller spectrum of potential uses than the antibodies themselves. In presently understood applications, such immunoglobulins are helpful in protein replacement therapy for globulin related anemia. In this context, an inability to bind to antigen is in fact helpful, as the therapeutic value of these proteins would be impaired by such functionality. At present, such non-specific antibodies are derivable in quantity only from myeloma cell cultures suitably induced. The present invention offers an alternative, more economical source. It also offers the opportunity of cancelling out specificity by manipulating the four chains of the tetramer separately.

A.2 General Structure Characteristics

The basic immunoglobin structural unit in vertebrate systems is now well understood (Edelman, G. M., *Ann. N.Y. Acad. Sci.,* 190: 5 (1971)). The units are composed to two identical light polypeptide chains of molecular weight approximately 23,000 daltons, and two identical heavy chains of molecular weight 53,000–70,000. The four chains are joined by disulfide bonds in a "Y" configuration wherein the light chains bracket the heavy chains starting at the mouth of the Y and continuing through the divergent region as shown in FIG. 1. The "branch" portion, as there indicated, is designated the Fab region. Heavy chains are classified as gamma, mu, alpha, delta, or epsilon, with some subclasses among them, and the nature of this chain, as it has a long constant region, determines the "class" of the antibody as IgG, IgM, IgA, IgD, or IgE. Light chains are classified as either kappa or lambda. Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells. However, if non-covalent association of the chains can be effected in the correct geometry, the aggregate will still be capable of reaction with antigen, or of utility as a protein supplement as a non-specific immunoglobulin.

The amino acid sequence runs from the N-terminal end at the top of the Y to the C-terminal end at the bottom of each chain. At the N-terminal end is a variable region which is specific for the antigen which elicited it, and is approximately 100 amino acids in length, there being slight variations between light and heavy chain and from antibody to antibody. The variable region is linked in each chain to a constant region which extends the remaining length of the chain. Linkage is seen, at the genomic level, as occuring through a linking sequence known currently as the "J" region in the light chain gene, which encodes about 12 amino acids, and as a combination of "D" region and "J" region in the heavy chain gene, which together encode approximately 25 amino acids.

The remaining portions of the chain are referred to as constant regions and within a particular class do not to vary with the specificity of the antibody (i.e., the antigen eliciting it).

As stated above, there are five known major classes of constant regions which determine the class of the immunoglobulin molecule (IgG, IgM, IgA, IgD, and IgE corresponding to $\gamma$, $\mu$, $\alpha$, $\delta$, and $\epsilon$ heavy chain constant regions). The constant region or class determines subsequent effector function of the antibody, including activation of complement (Kabat, E. A., *Structural Concepts in Immunology and Immunochemistry,* 2nd Ed., p. 413–436, Holt, Rinehart, Winston (1976)), and other cellular responses (Andrews, D. W., et al., *Clinical Immunobiology,* pp 1–18, W. B. Sanders (1980); Kohl, S., et al., *Immunology,* 48: 187 (1983)); while the variable region determines the antigen with which it will react.

B. Recombinant DNA Technology

Recombinant DNA technology has reach sufficient sophistication that it includes a repertoire of techniques for cloning and expression of gene sequences. Various DNA sequences can be recombined with some facility, creating new DNA entities capable of producing heterologous protein product in transformed microbes and cell cultures. The general means and methods for the in vitro ligation of various blunt ended or "sticky" ended fragments of DNA, for producing expression vectors, and for transforming organisms are now in hand.

DNA recombination of the essential elements (i.e., an origin of replication, one or more phenotypic selection characteristics, expression control sequence, heterologous gene insert and remainder vector) generally is performed outside the host cell. The resulting recombinant replicable expression vector, or plasmid, is introduced into cells by transformation and large quantities of the recombinant vehicle is obtained by growing the transformant. Where the gene is properly inserted with reference to portions which govern the transcription and translation of the encoded DNA message, the resulting expression vector is useful to produce the polypeptide sequence for which the inserted gene codes, a process referred to as "expression." The resulting product may be obtained by lysis, if necessary, of the host cell and recovery of the product by appropriate purifications from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment.

The art of maintaining cell or tissue cultures as well as microbial systems for studying genetics and cell physiology is well established. Means and methods are available for maintaining permanent cell lines, prepared by successive serial transfers from isolated cells. For use in research, such cell lines are maintained on a solid support in liquid medium, or by growth in suspension containing support nutriments. Scale-up for large preparations seems to pose only mechanical problems.

SUMMARY OF THE INVENTION

The invention relates to antibodies and to non-specific immunoglobulins (NSIs) formed by recombinant techniques using suitable host cell cultures. These antibodies and NSIs can be readily prepared in pure "monoclonal" form. They can be manipulated at the genomic level to produce chimeras of variants which draw their homology from species which differ from each other. They can also be manipulated at the protein level, since all four chains do not need to be produced by the same cell. Thus, there are a number of "types" of immunoglobulins encompassed by the invention.

First, immunoglobulins, particularly antibodies, are produced using recombinant techniques which mimic the amino acid sequence of naturally occuring antibodies produced by either mammalian B cells in situ, or by B cells fused with suitable immortalizing tumor lines, i.e., hybridomas. Second, the methods of this invention produced, and the invention is directed to, immunoglobulins which comprise polypeptides not hitherto found associated with each other in nature. Such reassembly is particularly useful in producing "hybrid" antibodies capable of binding more than one antigen; and in producing "composite" immunoglobuins wherein heavy and light chains of different origins essentially damp out specificity. Third, by genetic manipulation, "chimeric" antibodies can be formed wherein, for example, the variable regions, correspond to the amino acid sequence from one mammalian model system, whereas the constant region mimics the amino acid sequence of another. Again, the derivation of these two mimicked sequences may be from different species. Fourth, also by genetic manipulation, "altered" antibodies with improved specificity and other characteristics can be formed.

Two other types of immunoglobulin-like moieties may be produced: "univalent" antibodies, which are useful as homing carriers to target tissues, and "Fab proteins" which include only the "Fab" region of an immunoglobulin molecule i.e, the branches of the "Y". These univalent antibodies and Fab fragments may also be "mammalian" i.e., mimic mammalian amino acid sequences; novel assemblies of mammalian chains, or chimeric, where for example, the constant and variable sequence patterns may be of different origin. Finally, either the light chain or heavy chain alone, or portions thereof, produced by recombinant techniques are included in the invention and may be mammalian or chimeric.

In other aspects, the invention is directed to DNA which encodes the aforementioned NSIs, antibodies, and. portions thereof, as well as expression vectors or plasmids capable of effecting the production of such immunoglobulins in suitable host cells. It includes the host cells and cell cultures which result from transformation with these vectors. Finally, the invention is directed to methods of producing these NSIs and antibodies, and the DNA sequences, plasmids, and transformed cells intermediate to them.

BRIEF DESCRIPTION OF THE DRAWINGS

FIG. 1 is a representation of the general structure of immunoglobulins.

FIG. 2A and 2B show the detailed sequence of the cDNA insert of pK17G4 which encodes kappa anti CEA chain.

FIG. 3 shows the coding sequence of the fragment shown in FIG. 2, along with the corresponding amino acid sequence.

FIGS. 4A, 4B and 4C show the combined detailed sequence of the cDNA inserts of pγ298 and pγ11 which encode gamma anti CEA chain.

FIGS. 5A and 5B show the corresponding amino acid sequence encoded by the fragment in FIG. 4.

FIGS. 6 and 7 outline the construction of expression vectors for kappa and gamma anti-CEA chains respectively.

FIG. 10 shows a standard curve for ELISA assay of anti CEA activity.

FIGS. 11 and 12 show the construction of a plasmid for expression of the gene encoding a chimeric heavy chain.

FIG. 13 shows the construction of a plasmid for expression of the gene encoding the Fab region of heavy chain.

DETAILED DESCRIPTION

A. Definitions

Figure 8A:
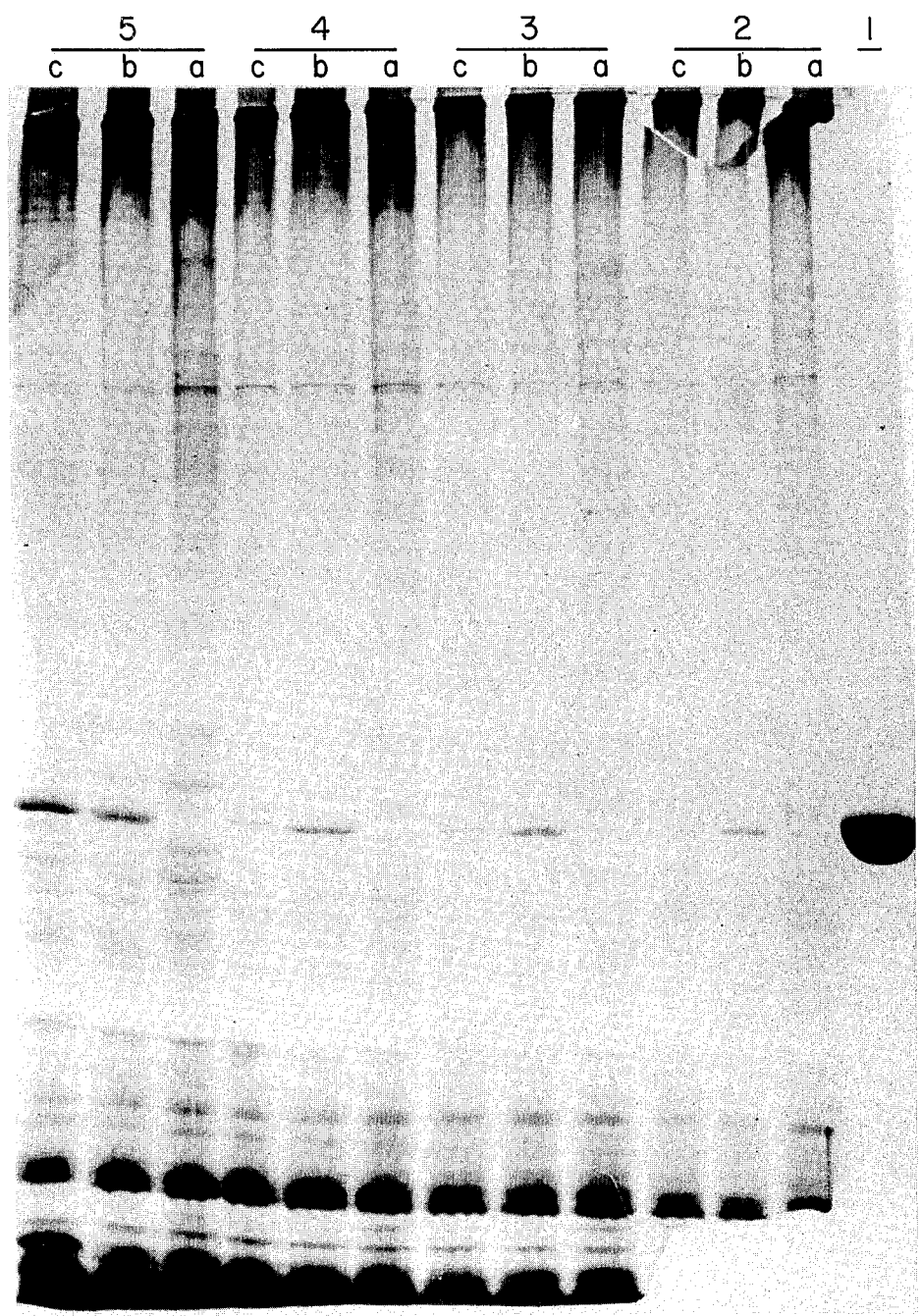
FIGS. 8A, 8B, and 8C show the results of sizing gels run on extracts of *E. coli* expressing the genes for gamma chain, kappa chain, and both kappa and gamma chains respectively.

As used herein, "antibodies" refers to tetramers or aggregates thereof which have specific immunoreactive activity, comprising light and heavy chains usually aggregated in the "Y" configuration of FIG. 1, with or without covalent linkage between them; "immunoglobulins" refers to such assemblies whether or not specific immunoreactive activity is a property. "Non-specific immunoglobulin" ("NSI") means those immunoglobulins which do not possess specificity—i.e., those which are not antibodies.

"Mammalian antibodies" refers to antibodies wherein the amino acid sequences of the chains are homologous with those sequences found in antibodies produced by mammalian systems, either in situ, or in hybridomas. These antibodies antibodies mimic antibodies which are otherwise capable of being generated, although in impure form, in these traditional systems.

"Hybrid antibodies" refers to antibodies wherein chains are separately homologous with reference mammalian antibody chains and represent novel assemblies of them, so that two different antigens are precipitable by the tetramer. In hybrid antibodies, one pair of heavy and light chain is homologous to antibodies raised against one antigen, while the other pair of heavy and light chain is homologous to those raised against another antigen. This results in the property of "divalence" i.e., ability to bind two antigens simultaneously. Such hybrids may, of course, also be formed using chimeric chains, as set forth below.

"Composite" immunoglobulins means those wherein the heavy and light chains mimic those of different species origins or specificities, and the resultant is thus likely to be a non-specific immunoglobulin (NSI), i.e.— lacking in antibody character.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source.

However, the definition is not limited to this particular example. It includes any antibody in which either or both of the heavy or light chains are composed of combinations of sequences mimicking the sequences in antibodies of different sources, whether these sources be differing classes, differing antigen respones, or differing species of origin and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation or to make other improvements in properties possessed by a particular constant region.

"Altered antibodies" means antibodies wherein the amino acid sequence has been varied from that of a mammalian or other vertebrate antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the constant region. Changes in the constant region will, in general, be made in order to improve the cellular process characteristics, such as complement fixation, interaction with membranes, and other effector functions. Changes in the variable region will be made in order to improve the antigen binding characteristics. The antibody can also be engineered so as to aid the specific delivery of a toxic agent according to the "magic bullet" concept. Alterations, can be made by standard recombinant techniques and also by oligonucleotide-directed mutagenesis techniques (Dalbadie-McFarland, et al *Proc. Natl. Acad. Sci.(USA)*, 79:6409 (1982)).

"Univalent antibodies" refers to aggregations which comprise a heavy chain/light chain dimer bound to the Fc (or stem) region of a second heavy chain. Such antibodies are specific for antigen, but have the additional desirable property of targeting tissues with specific antigenic surfaces, without causing its antigenic effectiveness to be impaired—i.e., there is no antigenic modulation. This phenomenon and the property of univalent antibodies in this regard is set forth in Glennie, M. J., et al., *Nature*, 295: 712 (1982). Univalent antibodies have heretofore been formed by proteolysis.

"Fab" region refers to those portions of the chains which are roughly equivalent, or analogous, to the sequences which comprise the Y branch portions of the heavy chain and to the light chain in its entirety, and which collectively (in aggregates) have been shown to exhibit antibody activity. "Fab protein", which protein is one of the aspects of the invention, includes aggregates of one heavy and one light chain (commonly known as Fab'), as well as tetramers which correspond to the two branch segments of the antibody Y, (commonly known as F(ab)$_2$), whether any of the above are covalently or non-covalently aggregated, so long as the aggregation is capable of selectively reacting with a particular antigen or antigen family. Fab antibodies have, as have univalent ones, been formed heretofore by proteolysis, and share the property of not eliciting antigen modulation on target tissues. However, as they lack the "effector" Fc portion they cannot effect, for example, lysis of the target cell by macrophages.

"Fab protein" has similar subsets according to the definition of the present invention as does the general term "antibodies" or "immunoglobulins". Thus, "mammalian" Fab protein, "hybrid" Fab protein "chimeric" Fab and "altered" Fab protein are defined analogously to the corresponding definitions set forth in the previous paragraphs for the various types of antibodies.

Individual heavy or light chains may of course be "mammalian", "chimeric" or "altered" in accordance with the above. As will become apparent from the detailed description of the invention, it is possible, using the techniques disclosed to prepare other combinations of the four-peptide chain aggregates, besides those specifically defined, such as hybrid antibodies containing chimeric light and mammalian heavy chains, hybrid Fab proteins containing chimeric Fab proteins of heavy chains associated with mammalian light chains, and so forth.

"Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As at present, such vectors are frequently in the form of plasmids, thus "plasmid" and "expression vector" are often used interchangeably. However, the invention is intended to include such other forms of expression vectors which serve equivalent functions and which may, from time to time become known in the art.

"Recombinant host cells" refers to cells which have been transformed with vectors constructed using recombinant DNA techniques. As defined herein, the antibody or modification thereof produced by a recombinant host cell is by virtue of this transformation, rather than in such lesser amounts, or more commonly, in such less than detectable amounts, as would be produced by the untransformed host.

In descriptions of processes for isolation of antibodies from recombinant hosts, the terms "cell" and "cell culture" are used interchangeably to denote the source of antibody unless it is clearly specified otherwise. In other words, recovery of antibody from the "cells" may mean either from spun down whole cells, or from the cell culture containing both the medium and the suspended cells.

B. Host Cell Cultures and Vectors

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537). These examples are, of course, intended to be illustrative rather than limiting.

Prokaryotes may also be used for expression. The aforementioned strains, as well as *E. coli* W3110 (F$^{31}$, λ$^-$, prototrophic, ATTC No. 27325), bacilli such as *Bacillus subtilus*, and other enterobacteriaceae such as *Salmonella typhimurium* or *Serratia marcesans*, and various *Pseudomonas* species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., *Gene* 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, *Nature*, 275: 615 (1978); Itakura, et al, *Science*, 198: 1056 (1977); (Goeddel, et al *Nature* 281: 544 (1979)) and a tryptophan (trp) promoter system (Goeddel, et al, *Nucleic Acids Res.*, 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, *Cell* 20: 269 (1980)).

In addition to prokaryates, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, (Stinchcomb, et al, *Nature*, 282: 39 (1979); Kingsman et al, *Gene*, 7: 141 (1979); Tschemper, et al, *Gene*, 10: 157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics*, 85: 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255: 2073 (1980)) or other glycolytic enzymes (Hess, et al, *J. Adv. Enzyme Reg.*, 7: 149 (1968); Holland, et al, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, an enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However interest has been greatest in vertebrate cells, and propogation of vertebrate cells in culture (tissue culture) has become a routine procedure in recent years (*Tissue Culture*, Academic Pres, Kruse and Patterson, editors (1973)). Examlples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature*, 273: 113 (1978)) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

It will be understood that this invention, although described herein in terms of a preferred embodiment, should not be construed as limited to those host cells, vectors and expression systems exemplified.

C. Methods Employed

C.1 Transformation

If cells without formidable cell wall barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al *Proc. Natl. Acad. Sci. (USA)*, 69: 2110 (1972).

C.2 Vector Construction

Construction of suitable vectors containing the desired coding and control sequences employ standard ligation techniques. Isolated plasmids or DNA fragments are cleaved, tailored, and religated in the form desired to form the plasmids required. The methods employed are not dependent on the DNA source, or intended host.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.*, 8: 4057 (1980) incorporated herein by reference.

For ligation, approximately equimolar amounts of the desired components, suitably end tailored to provide correct matching are treated with about 10 units T4 DNA ligase per 0.5 μg DNA. (When cleaved vectors are used as components, it may be useful to prevent religation of the cleaved vector by pretreatment with bacterial alkaline phosphatase.)

In the examples described below correct ligations for plasmid construction are confirmed by transforming *E. coli* K12 strain 294 (ATCC 31446) with the ligation mixture. Successful transformants were selected by ampicillin or tetracycline resistance depending on the mode of plasmid construction. Plasmids from the transformants were then prepared, analyzed by restriction and/or sequenced by the method of Messing, et al, *Nucleic Acids Res.*, 9: 309 (1981) or by the method of Maxam, et al, *Methods in Enzymology*, 65: 499 (1980).

D. Outline of Procedures

D.1 Mammalian Antibodies

The first type of antibody which forms a part of this invention, and is prepared by the methods thereof, is "mammalian antibody"-one wherein the heavy and light chains mimic the amino acid sequences of an antibody otherwise produced by a mature mammalian B lymphocyte either in situ or when fused with an immortalized cell as part of a hybridoma culture. In outline, these antibodies are produced as follows:

Messenger RNA coding for heavy or light chain is isolated from a suitable source, either mature B cells or a hybridoma culture, employing standard techniques of RNA isolation, and the use of oligo-dT cellulose chromatography to segregate the poly-A mRNA.. The poly-A mRNA may, further, be fractionated to obtain sequences of sufficient size to code for the amino acid sequences in the light or heavy chain of the desired antibody as the case may be.

A cDNA library is then prepared from the mixture of mRNA using a suitable primer, preferably a nucleic acid sequence which is characteristic of the desired cDNA. Such a primer may be hypothesized and synthesized based on the amino acid sequence of the antibody if the sequence is known. In the alternative cDNA from unfractionated poly-A mRNA from a cell line producing the desired antibody or poly-dT may also be used. The resulting cDNA is optionally size fractionated on polyacrylamide gel and then extended with, for example, dC residues for annealing with pBR322 or other suitable cloning vector which has been cleaved by a suitable restriction enzyme, such as Pst I, and extended with dG residues. Alternative means of forming cloning vectors containing the cDNA using other tails and other cloning vector remainder may, of course, also be used but the foregoing is a standard and preferable choice. A suitable host cell strain, typically *E. coli*, is transformed with the annealed cloning vectors, and the successful transformants identified by means of, for example, tetracycline resistance or other phenotypic characteristic residing on the cloning vector plasmid.

Successful transformants are picked and transferred to microtiter dishes or other support for further growth and preservation. Nitrocellulose filter imprints of these growing cultures are then probed with suitable nucleotide sequences containing bases known to be complementary to desired sequences in the cDNA. Several types of probe may be used, preferably synthetic single stranded DNA sequences labeled by kinasing with ATP$^{32}$. The cells fixed to the nitrocellulose filter are lysed, the DNA denatured, and then fixed before reaction with kinased probe. Clones which successfully hybridize are detected by contact with a photoplate, then plasmids from the growing colonies isolated and sequenced by means known in the art to verify that the desired portions of the gene are present.

The desired gene fragments are excised and tailored to assure appropriate reading frame with the control segments when inserted into suitable expression vectors. Typically, nucleotides are added to the 5' end to include a start signal and a suitably positioned restriction endonuclease site.

The tailored gene sequence is then positioned in a vector which contains a promoter in reading frame with the gene and compatible with the proposed host cell. A number of plasmids such as those described in U.S. Pat. Nos. 4,663,283 and 4,456,748 and pending U.S. Ser. No. 291,892, have been described which already contain the appropriate promoters, control sequences, ribosome binding sites, and transcription termination sites, as well as convenient markers.

In the present invention, the gene coding for the light chain and that coding for the heavy chain are recovered separately by the procedures outlined above. Thus they may be inserted into separate expression plasmids, or together in the same plasmid, so long as each is under suitable promoter and translation control.

The expression vectors constructed above are then used to transform suitable cells. The light and heavy chains may be transformed into separate cell cultures, either of the same or of differing species; separate plasmids for light and heavy chain may be used to co-transform a single cell culture, or, finally, a single expression plasmid containing both genes and capable of expressing the genes for both light and heavy chain may be transformed into a single cell culture.

Regardless of which of the three foregoing options is chosen, the cells are grown under conditions appropriate to the production of the desired protein. Such conditions are primarily mandated by the type of promoter and control systems used in the expression vector, rather than by the nature of the desired protein. The protein thus produced is then recovered from the cell culture by methods known in the art, but choice of which is necessarily dependent on the form in which the protein is expressed. For example, it is common for mature heterologous proteins expressed in *E. coli* to be deposited within the cells as insoluble particles which require cell lysis and solubilization in denaturant to permit recovery. On the other hand, proteins under proper synthesis circmstances, in yeast and bacterial strains, can be secreted into the medium (yeast and gram positive bacteria) or into the periplasmic space (gram negative bacteria) allowing recovery by less drastic procedures. Tissue culture cells as hosts also appear, in general, to permit reasonably facile recovery of heterologous proteins.

When heavy and light chain are coexpressed in the same host, the isolation procedure is designed so as to recover reconstituted antibody. This can be accomplished in vitro as described below, or might be possible in vivo in a microorganism which secretes the IgG chains out of the reducing environment of the cytoplasm. A more detailed description is given in D.2 below.

D.2 Chain Recombination Techniques

The ability of the method of the invention to produce heavy and light chains or portions thereof, in isolation from each other offers the opportunity to obtain unique and unprecedented assemblies of immunoglobulins, Fab regions, and univalent antibodies. Such preparations require the use of techniques to reassemble isolated chains. Such means are known in the art, and it is, thus, appropriate to review them here.

While single chain disulfide bond containing proteins have been reduced and reoxidized to regenerate in high yield native structure and activity (Freedman, R. B., et al. In *Enzymology of Post Translational Modification of Proteins*, I: 157–212 (1980) Academic Press, NY.), proteins which consist of discontinuous polypeptide chains held together by disulfide bonds are more difficult to reconstruct in vitro after reductive cleavage. Insulin, a cameo case, has received much experimental attention over the years, and can now be reconstructed so efficiently that an industrial process has been built around it (Chance, R. E., et al., In *Peptides: Proceedings of the Seventh Annual American Peptide Symposium* (Rich, D. H. and Gross, E., eds.) 721–728, Pierce Chemical Co., Rockford, IL. (1981)).

Immunoglobulin has proved a more difficult problem than insulin. The tetramer is stabilized intra and intermolecularly by 15 or more disulfide bonds. It has been possible to recombine heavy and light chains, disrupted by cleavage of only the interchain disulfides, to regain antibody activity even without restoration of the interchain disulfides (Edelman, G. M., et al., *Proc. Natl. Acad. Sci (USA)* 50: 753 (1963)). In addition, active fragments of IgG formed by proteolysis (Fab fragments of ~50,000 MW) can be split into their fully reduced heavy chain and light chain components and fairly efficiently reconstructed to give active antibody (Haber, E., *Proc. Natl. Acad. Sci. (USA)* 52: 1099 (1964); Whitney, P. L., et al., *Proc. Natl. Acad. Sci. (USA)* 53: 524 (1965)). Attempts to reconstitute active antibody from fully reduced native IgG have been largely unsuccessful, presumably due to insolubility of the reduced chains and of side products or intermediates in the refolding pathway (see discussion in Freedman, M. H., et al., *J. Biol. Chem.* 241: 5225 (1966)). If, however, the immunoglobulin is randomly modified by polyalanylation of its lysines before complete reduction, the separated chains have the ability to recover antigen-combining activity upon reoxidation (ibid).

A particularly suitable method for immunoglobulin reconstitution is derivable from the now classical insulin recombination studies, wherein starting material was prepared by oxidative sulfitolysis, thus generating thiol-labile S-sulfonate groups at all cysteines in the protein, non-reductively breaking disulfides (Chance et al. (supra)). Oxidative sulfitolysis is a mild disulfide cleavage reaction (Means, G. E., et al., *Chemical Modification of Proteins*, Holden-Day, San Francisco (1971) which is sometimes more gentle than reduction (Wetzel, R., *Biochemistry*, submitted (1983)), and which generates derivatives which are stable until exposed to mild reducing agent at which time disulfide reformation can occur via thiol-disulfide interchange (Morehead, H., et al. *Biochemistry*, in press, (1983)). In the present invention the heavy and light chain S-sulfonates generated by oxidative sulfitolysis were reconstituted utilizing both air oxidation and thiol-disulfide interchange to drive disulfide bond formation. The general procedure is set forth in detail in U.S. Pat. No. 4,599,197 incorporated herein by reference.

D.3 Variants Permitted by Recombinant Technology

Using the techniques described in paragraphs D.1 and D.2, additional operations which were utilized to gain efficient production of mammalian antibody can be varied in quite straightforward and simple ways to produce a great variety of modifications of this basic antibody form. These variations are inherent in the use of recombinant technology, which permits modification at a genetic level of amino acid sequences in normally encountered mammalian immunoglobulin chains, and the great power of this approach lies in its ability to achieve these variations, as well as in its potential for economic and specific production of desired scarce, and often contaminated, molecules. The variations also inhere in the ability to isolate production of individual chains, and thus create novel assemblies.

Briefly, since genetic manipulations permit reconstruction of genomic material in the process of construction of expression vectors, such reconstruction can be manipulated to produce new coding sequences for the components of "natural" antibodies or immunoglobulins. As discussed in further detail below, the coding sequence for a mammalian heavy chain may not be derived entirely from a single source or a single species, but portions of a sequence can be recovered by the techniques described in D.1 from differing pools of mRNA, such as murine-murine hybridomas, human-murine hybridomas, or B cells differentiated in response to a series of antigen challenges. The desired portions of the sequences in each case can be recovered using the probe and analysis techniques described in D.1, and recombined in an expression vector using the same ligation procedures as would be employed for portions of the same model sequence. Such chimeric chains can be constructed of any desired length; hence, for example, a complete heavy chain can be constructed, or only sequence for the Fab region thereof.

The additional area of flexibility which arises from the use of recombinant techniques results from the power to produce heavy and light chains or fragments thereof in separate cultures or of unique combinations of heavy and light chain in the same culture, and to prevent reconstitution of the antibody or immunoglobulin aggregation until the suitable components are assembed. Thus, while normal antibody production results automatically in the formation of "mammalian antibodies" because the light and heavy chain portions are constructed in response to a particular determinant in the same cell, the methods of the present invention present the opportunity to assemble entirely new mixtures. Somewhat limited quantities of "hybrid" antibodies have been produced by "quadromas" i.e., fusions of two hybridoma cell cultures which permit random assemblies of the heavy and light chains so produced.

The present invention permits a more controlled assembly of desired chains, either by mixing the desired chains in vitro, or by transforming the same culture with the coding sequences for the desired chains.

D.4 Composite Immunoglobulins

The foregoing procedure, which describes in detail the recombinant production of mammalian antibodies is employed with some modifications to construct the remaining types of antibodies or NSIs encompassed by the present invention. To prepare the particular embodiment of composite non-specific immunoglobulin wherein the homology of the chains corresponds to the sequences of immunoglobulins of different specificities, it is of course, only necessary to prepare the heavy and light chains in separate cultures and reassemble them as desired.

For example, in order to make an anti-CEA light chain/anti-hepatitis heavy chain composite antibody, a suitable source for the mRNA used as a template for the light chain clone would comprise, for instance, the anti CEA producing cell line of paragraph E.1. The mRNA corresponding to heavy chain would be derived from B cells raised in response to hepatitis infection or from hybridoma in which the B cell was of this origin. It is clear that such composites can be assembled using the methods of the invention almost at will, and are limited only by available sources of mRNA suitable for use as templates for the respective chains. All other features of the process are similar to those described above.

D.5 Hybrid Antibodies

Hybrid antibodies are particularly useful as they are capable of simultaneous reaction with more than one antigen. Pairs of heavy and light chains corresponding to chains of antibodies for different antigens, such as those set forth in paragraph D.4 are prepared in four separate cultures, thus preventing premature assembly of the tetramer. Subsequent mixing of the four separately prepared peptides then permits assembly into the desired tetramers. While random aggregation may lead to the formation of considerable undesired product, that portion of the product in which homologous light and heavy chains are bound to each other and mismatched to another pair gives the desired hybrid antibody.

D.6 Chimeric Antibodies

For construction of chimeric antibodies (wherein, for example, the variable sequences are separately derived from the constant sequences) the procedures of paragraph D.1 and D.2 are again applicable with appropriate additions and modifications. A preferred procedure is to recover desired portions of the genes encoding for parts of the heavy and light chains from suitable, differing, sources and then to religate these fragments using restriction endonucleases to reconstruct the gene coding for each chain.

For example, in a particular preferred chimeric construction, portions of the heavy chain gene and of the light chain gene which encode the variable sequences of antibodies produced by a murine hybridoma culture are recovered and cloned from this culture and gene fragments encoding the constant regions of the heavy and light chains for human antibodies recovered and cloned from, for example, human myeloma cells. Suitable restriction enzymes may then be used to ligate the variable portions of the mouse gene to the constant regions of the human gene for each of the two chains. The chimeric chains are produced as set forth in D.1, aggregated as set forth in D.2 and used in the same manner as the non-chimeric forms. Of course, any splice point in the chains can be chosen.

D.7 Altered Antibodies

Altered antibodies present, in essence, an extension of chimeric ones. Again, the techniques of D.1 and D.2 are applicable; however, rather than splicing portions of the chain(s), suitable amino acid alterations, deletions or additions are made using available techniques such as mutagenesis (supra). For example, genes which encode antibodies having diminished complement fixation properties, or which have enhanced metal binding capacities are prepared using such techniques. The latter type may, for example, take advantage of the known gene sequence encoding metalothionein II (Karin, M., et al., *Nature,* 299: 797 (1982)). The chelating properties of this molecular fragment are useful in carrying heavy metals to tumor sites as an aid in tumor imaging (Scheinberg, D. A., et al., *Science,* 215: 19 (1982).

D.8 Univalent Antibodies

In another preferred embodiment, antibodies are formed which comprise one heavy and light chain pair coupled with the Fc region of a third (heavy) chain. These antibodies have a particularly useful property. They can, like ordinary antibodies, be used to target antigenic surfaces of tissues, such as tumors, but, unlike ordinary antibodies, they do not cause the antigenic surfaces of the target tissue to retreat and become non-receptive. Ordinary antibody use results in aggregation and subsequent inactivation, for several hours, of such surface antigens.

The method of construction of univalent antibodies is a straightforward application of the invention. The gene for heavy chain of the desired Fc region is cleaved by restriction enzymes, and only that portion coding for the desired Fc region expressed. This portion is then bound using the technique of D.2 to separately produced heavy chain the desired pairs separated from heavy/heavy and Fc/Fc combinations, and separately produced light chain added. Pre-binding of the two heavy chain portions thus diminishes the probability of formaion of ordinary antibody.

D.9 Fab Protein

Similarly, it is not necessary to include the entire gene for the heavy chain portion. All of the aforementioned variations can be superimposed on a procedure for Fab protein production and the overall procedure differs only in that that portion of the heavy chain coding for the amino terminal 220 amino acids is employed in the appropriate expression vector.

E. Specific Examples of Preferred Embodiments

The invention has been described above in general terms and there follow several specific examples of embodiments which set forth details of experimental procedure in producing the desired antibodies. Example E.1 sets forth the general procedure for preparing anti CEA antibody components, i.e. for a "mammalian antibody". Example E.3 sets forth the procedure for reconstitution and thus is applicable to preparation of mammalian, composite, hybrid and chimeric immunoglobulins, and Fab proteins and univalent antibodies. Example E.4 sets forth the procedure for tailoring the heavy or light chain so that the variable and constant regions may be derived from different sources. Example E.5 sets forth the method of obtaining a shortened heavy chain genome which permits the production of the Fab regions and, in an analogous manner, Fc region.

The examples set forth below are included for illustrative purposes and do not limit the scope of the invention.

E.1 Construction of Expression Vectors for Murine anti-CEA Antibody Chains and Peptide Synthesis Carcinoembryonic antigen (CEA) is associated with the surface of certain tumor cells of human origin (Gold, P., et al., *J. Exp. Med.*, 122: 467 (1965)). Antibodies which bind to CEA (anti-CEA antibodies) are useful in early detection of these tumors (Van Nagell, T. R., et al., *Cancer Res.* 40: 502 (1980)), and have the potential for use in treatment of those human tumors which appear to support CEA at their surfaces. A mouse hybridoma cell line which secretes anti-CEA antibodies of the Ig$\gamma_1$ class, CEA.66-E3, has been prepared as described by Wagener, C, et al., *J. Immunol.* (in press) which is incorporated herein by reference, and was used as mRNA source. The production of anti CEA antibodies by this cell line was determined. The N-terminal sequences of the antibodies produced by these cells was compared with those of monoclonal anti CEA as follows. Purified IgG was treated with PCAse (Podell, D. N., et al., BBRC 81: 176 (1978)), and then dissociated in 6M guanidine hydrochloride, 10 mM 2-mercaptoethanol (1.0 mg of immunoglobulin, 5 min, 100° C. water bath). The dissociated chains were separated on a Waters Associates alkyl phenyl column using a liner gradient from 100 percent A (0.1 percent TFA-water) to 90 percent B (TFA/H$_2$O/MeCN 0.1/9.9/90) at a flow rate of 0.8 ml/min. Three major peaks were eluted and analyzed on SDS gels by silver staining. The first two peaks were pure light chain (MW 25,000 daltons), the third peak showed a (7:3) mixture of heavy and light chain. 1.2 nmoles of light chain were sequenced by the method of Shively, J. E., *Methods in Enzymology*, 79: 31 (1981), with an NH$_2$-terminal yield of 0.4 nmoles. A mixture of heavy and light chains (3 nmoles) was also sequenced, and sequence of light chain was deducted from the double sequence to yield the sequence of the heavy chain.

In the description which follows, isolation and expression of the genes for the heavy and light chains for anti CEA antibody produced by CEA.66-E3 are described. As the constant regions of these chains belong to the gamma and kappa families, respectively, "light chain" and "kappa chain", and "heavy chain" and "gamma chain", respectively, are used interchangeably below.

E.1.1 Isolation of Messenger RNA for Anti CEA Light and Heavy (Kappa and Gamma) Chains Total RNA for CEA.66-E3 cells was extracted essentially as reported by Lynch et al, *Virology*, 98: 251 (1979). Cells were pelleted by centrifugation and approximately 1 g portions of pellet resuspended in 10 ml of 10 mM NaCl, 10 mM Tris HCl (pH 7.4), 1.5 mM MgCl$_2$. The resuspended cells were lysed by addition of non-ionic detergent NP-40 to a final concentration of 1 percent, and nuclei removed by centrifugation. After addition of SDS (pH 7.4) to 1 percent final concentration, the supernatant was extracted twice with 3 ml portions of phenol (redistilled)/chloroform:isoamyl alcohol 25:1 at 4° C. The aqueous phase was made 0.2M in NaCl and total RNA was precipitated by addition of two volumes of 100 percent ethanol and overnight storage at −20° C. After centrifugation, polyA mRNA was purified from total RNA by oligo-dT cellulose chromatography as described by Aviv and Leder, *Proc. Nat'l. Acad. Sci* (USA), 69: 1408 (1972). 142 μg of polyA mRNA was obtained from 1 g cells.

E.1.2 Preparation of *E. coli* Colony Library Containing Plasmids with Heavy and Light DNA Sequence Inserts 5 μg of the unfractionated polyA mRNA prepared in paragraph E.1.1 was used as template for oligo-dT primed preparation of double-stranded (ds) cDNA by standard procedures as described by Goeddel et al., *Nature* 281: 544 (1979) and Wickens et al., *J. Biol. Chem.* 253: 2483 (1978) incorporated herein by reference. The cDNA was size fractionated by 6 percent polyacrylamide gel electrophoresis and 124 ng of ds cDNA greater than 600 base pairs in length was recovered by electroelution. A 20 ng portion of ds cDNA was extended with deoxy C residues using terminal deoxynucleotidyl transferase as described in Chang et al., *Nature* 275: 617 (1978) incorporated herein by reference, and annealed with 200 ng of the plasmid pBR322 (Bolivar et al., *Gene* 2: 95 (1977)) which had been cleaved with Pst I and tailed with deoxy G. Each annealed mixture was then transformed into *E. coli* K12 strain 294 (ATCC No. 31446). Approximately 8500 ampicillin sensitive, tetracycline resistant transformants were obtained.

E.1.3 Preparation of Synthetic Probes

The 14 mer, 5′GGTGGGAAGATGGA 3′ complementary to the coding sequence of constant region for mous MOPC21 kappa chain which begins 25 basepairs 3′ of the variable region DNA sequence was used as kappa chain probe. A 15 mer, 5′GACCAGGCATCCCAG 3′, complementary to a coding sequence located 72 basepairs 3′ of the variable region DNA sequence for mouse MOPC21 gamma chain was used to probe gamma chain gene.

Both probes were synthesized by the phosphotriester method described in German Offenlegungschrift No. 2644432, incorporated herein by reference, and made radioactive by kinasing as follows: 250 ng of deoxyoligonucleotide were combined in 25 μl of 60 mM Tris HCl (pH 8), 10 mM MgCl$_2$, 15 mM beta-mercaptoethanol, and 100 μCi ($\gamma$-$^{32}$P) ATP (Amersham, 5000 Ci/mMole). 5 units of T4 polynucleotide kinase were added and the reaction was allowed to proceed at 37° C. for 30 minutes and terminated by additon of EDTA to 20 mM.

E.1.4 Screening of Colony Library for Kappa or Gamma Chain Sequences

~2000 colonies prepared as described in paragraph E.1.2 were individually inoculated into wells of microtitre dishes containing LB (Miller, Experiments in Molecular Genetics, p. 431-3, Cold Spring Harbor Lab., Cold Spring Harbor, N.Y. (1972))+5 μg/ml tetracycline and stored at −20° C. after addition of DMSO to 7 percent. Individual colonies from this library were transferred to duplicate sets of Schleicher and Schuell BA85/20 nitrocellulose filters and grown on agar plates containing LB+5 μg/ml tetracycline. After ~10 hours growth at 37° C. the colony filters were transferred to agar plates containing LB+5 μg/ml tetracycline and 12.5 μg/ml chloramphicol and reincubated overnight at 37° C. The DNA from each colony was then denatured and fixed to the filter by a modification of the Grunstein-Hogness procedure as described in Grunstein et al., *Proc. Natl. Acad. Sci. (USA)* 72: 3961 (1975), incorporated herein by reference. Each filter was floated for 3 minutes on 0.5N NaOH, 1.5M NaCl to lyse the colonies and denature the DNA then neutralized by floating for 15 minutes on 3M NaCl, 0.5M Tris HCl (pH 7.5). The filters were then floated for an additional 15 minutes on 2×SSC, and subsequently baked for 2 hours in an 80° C. vacuum oven. The filters were prehybridized for ~2 hours at room temperature in 0.9M NaCl, 1× Denhardts, 100 mM Tris HCl (pH 7.5), 5 mM Na-EDTA, 1 mM ATP, 1M sodium phosphate (dibasic), 1 mM sodium pyrophosphate, 0.5 percent NP-40, and 200 μg/ml *E. coli* t-RNA, and hybridized in the same solution overnight, essentially as described by Wallace et al. *Nucleic Acids Research* 9: 879 (1981) using ~40×$10^6$ cpm of either the kinased kappa or gamma probe described above.

After extensive washing at 37° C. in 6X SSC, 0.1 percent SDS, the filters were exposed to Kodak XR-5 X-ray film with DuPont Lightning-Plus intensifying screens from 16-24 hours at −80° C. Approximately 20 colonies which hybridized with kappa chain probe and 20 which hybridized with gamma chain probe were characterized.

E.1.5 Characterization of Colonies which Hybridize to Kappa DNA Sequence Probe

Plasmid DNAs isolated from several different transformants which hybridized to kappa chain probe were cleaved with Pst I and fractionated by polyacrylamide gel electrophoresis (PAGE). This analysis demonstrated that a number of plasmid DNAs contained cDNA inserts large enough to encode full length kappa chain. The complete nucleotide sequence of the cDNA insert of one of these plasmids was determined by the dideoxynucleotide chain termination method as described by Smith, *Methods Enzymol.* 65, 560 (1980) incorporated herein by reference after subcloning restriction endonuclease cleavage fragments into M13 vectors (Messing et al., *Nucleic Acids Research* 9: 309 (1981). FIG. 2 shows the nucleotide sequence of the cDNA insert of pK17G4 and FIG. 3 shows the gene sequence with the corresponding amino acid sequence. Thus, the entire coding region of mouse anti-CEA kappa chain was isolated on this one large DNA fragment. The amino acid sequence of kappa chain, deduced from the nucleotide sequence of the pK17G4 cDNA insert, corresponds perfectly with the first 23 N-terminal amino acids of mature mouse anti-CEA kappa chain as determined by amino acid sequence analysis of purified mouse anti-CEA kappa chain. The coding region of pK17G4 contains 27 basepairs or 9 amino acids of the presequence and 642 basepairs or 214 amino acids of the mature protein. The mature unglycosylated protein (MW 24,553) has a variable region of 119 amino acids, including the J1 joining region of 12 amino acids, and a constant region of 107 amino acids. After the stop codon behind amino acid 215 begins 212 basepairs of 3' untranslated sequence up to the polyA addition. The kappa chain probe used to identify pK17G4 hybridizes to nucleotides 374–388 (FIG. 2).

E.1.6. Characterization of Colonies which Hybridize to Gamma 1 DNA Probe

Plasmid DNA isolated from several transformants positive for hybridization with the heavy chain gamma 1 probe was subjected to Pst I restriction endonuclease analysis as described in E.1.5. Plasmid DNAs demonstrating the largest cDNA insert fragments were selected for further study. Nucleotide sequence coding for mouse heavy (gamma-1) chain, shows an NcoI restriction endonuclease cleavage site near the junction between variable and constant region. Selected plasmid DNAs were digested with both PstI and NcoI and sized on polyacrylamide. This analysis allowed identification of a number of plasmid DNAs that contain NcoI restriction endonuclease sites, although none that demonstrate cDNA insert fragments large enough to encode the entire coding region of mouse anti-CEA heavy chain.

In one plasmid isolated, pγ298 the cDNA insert of about 1300 bp contains sequence information for the 5' untranslated region, the signal sequence and the N-terminal portion of heavy chain. Because pγ298 did not encode the C-terminal sequence for mouse anti-CEA gamma 1 chain, plasmid DNA was isolated from other colonies and screened with PstI and NcoI. The C-terminal region of the cDNA insert of pγ11 was sequenced and shown to contain the stop codon, 3' untranslated sequence and that portion of the coding sequence missing from p γ298.

FIG. 4 presents the entire nucleotide sequence of mouse anti-CEA heavy chain (as determined by the dideoxynucleotide chain termination method of Smith, *Methods Enzymol.*, 65: 560 (1980)) and FIG. 5 includes the translated sequence.

The amino acid sequence of gamma 1 (heavy chain) deduced from the nucleotide sequence of the pγ298 cDNA insert corresponds perfectly to the first 23 N-terminal amino acids of mature mouse anti-CEA gamma 1 chain as determined by amino acid sequence analysis of purified mouse anti-CEA gamma-1 chain. The coding region consists of 57 basepairs or 19 amino acids of presequences and 1346 basepairs or 447 amino acids of mature protein. The mature unglycosolated protein (MW 52,258) has a variable region of 135 amino acids, including a D region of 12 amino acids, and a J4 joining region of 13 amino acids. The constant region is 324 amino acids. After the stop codon behind amino acid 447 begins 96 bp of 3' untranslated sequences up to the polyA addition. The probe used to identify pγ298 and pγ11 hybridized to nucleotides 528–542 (FIG. 4).

E.1.7 Construction of a Plasmid For Direct Expression of Mouse Mature Anti-CEA Kappa Chain Gene, pKCEAtrp207-1*

FIG. 6 illustrates the construction of pKCEAtrp207-1*

First, an intermediate plasmid pHGH207-1*, having a single trp promoter, was prepared as follows:

The plasmid pHGH 207 (described in U.S. Pat. No. 4,663,283), was used to prepare pHGH 207-1, pHGH 207 was digested with BamHI, followed by partial digestion with EcoRI. The largest fragment, which contains the entire trp promoter, was isolated and ligated to the largest EcoRI-BamHI fragment from pBR322, and the ligation mixture used to transform *E. coli* 294. Tet and Amp resistant colonies were isolated, and most of them contained pHGH207-1. pHGH207-1* which lacks the EcoR1 site between the $amp^R$ gene and the trp promoter, was obtained by partial digestion of pHGH207-1 (de Boer et al., *Promoters*, Rodriquez et al. Eds. (1982), pp. 462–481 U.S. Pat. No. 4,663,283) with EcoR I, filling in the ends with Klenow and dNTPs, and religation.

5 μg of pHGH207-1* was digested with EcoRI, and the ends extended to blunt ends using 12 units of DNA Polymerase I in a 50 μl reaction containing 60 mM NaCl, 7 mM MgCl$_2$, 7 mM Tris HCl (pH 7.4) and 1 mM in each dNTP at 37° C. for 1 hour, followed; by extraction with phenol/CHCl$_3$ and precipitation with ethanol. The precipitated DNA was digested with BamH I, and the large vector fragment (fragment 1) purified using 5 percent polyacrylamide gel electrophoresis, electroelution, phenol/CHCl$_3$ extraction and ethanol precipitation.

The DNA was resuspended in 50 μl of 10 mM Tris pH 8, 1 mM EDTA and treated with 500 units Bacterial Alkaline Phosphatase (BAP) for 30' at 65° followed by phenol/CHCl$_3$ extraction and ethanol precipitation.

A DNA fragment containing part of the light chain sequence was prepared as follows: 7 μg of pK17G4 DNA was digested with Pst I and the kappa chain containing cDNA insert was isolted by 6 percent gel electrophoresis, and electroelution. After phenol/CHCl$_3$ extraction, ethanol precipitaion and resuspensionin water, this fragment was digested with Ava II. The 333 bp Pst I-Ava II DNA fragment was isolated and purified from a 6 percent polyacrylamide gel.

A 15 nucleotide DNA primer was synthesized by the phosphotriester method G.O. 2,644,432 (supra) and has the following sequence:

```
        Met Asp Ile Val Met
    5' ATG GAC ATT GTT ATG 3'
```

The 5' methionine serves as the initiation codon. 500 ng of this primer was phosphorylated at the 5' end with 10 units T4 DNA kinase in 20 μl reaction containing 0.5 mM ATP. ~200 ng of the Pst I-Ava II DNA fragment was mixed with the 20 μl of the phosphorylated primer, heated to 95° C. for 3 minutes and quick frozen in a dry-ice ethanol bath. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C. this primer repair reaction was phenol/CHCl$_3$ extracted, ethanol precipitated, and digested to completion with Sau 3A. The reaction mixture was then electrophoresed on a 6 percent polyacrylamide gel and ~50 ng of the 182 basepair amino-terminal blunt-end to Sau 3A fragment (fragment 2) was obtained after electroelution.

100 ng of fragment 1 (supra) and 50 ng of fragment 2 were combined in 20 μl of 20 mM Tris HCl (pH 7.5), 10 mM MgCl$_2$, 10 mM DTT, 2.5 mM ATP and 1 unit of T4 DNA ligase. After overnight ligation at 14° C. the reaction was transformed into *E. coli* K12 strain 294. Restriction endonuclease digestion of plasmid DNA from a number of ampicillin resistant transformants indicated the proper construction and DNA sequene analysis proved the desired nucleotide sequence through the initiation codon of this new plasmid, pKCEAInt1 (FIG. 6).

The remainder of the coding sequence of the kappa light chain gene was prepared as follows:

The Pst I cDNA insert fragment from 7 μg of K17G4 DNA was partially digested with Ava II and the Ava II cohesive ends were extended to blunt ends in a DNA Polymerase I large fragment reaction. Following 6 percent polyacrylamide gel electrophoresis the 686 basepair Pst I to blunt ended Ava II DNA fragment was isolated, purified and subjected to Hpa II restriction endonuclease digestion. The 497 basepair Hpa II to blunt ended Ava II DNA fragment (fragment 3) was isoated and purified after gel electrophoresis.

10 μg of pKCEAInt1 DNA was digested with Ava I, extended with DNA polymerase I large fragment, and digested with Xba I. Both the large blunt ended Ava I to Xba I vector fragment and the small blunt ended Ava I to Xba I fragment were isolated and purified from a 6 percent polyacrylamide gel after electrophoresis. The large vector fragment (fragment 4) was treated with Bacterial Alkaline Phosphatase (BAP), and the small fragment was digested with Hpa II, electrophoresed on a 6 percent polyacrylamide and the 169 basepair Xba I-Hpa II DNA fragment (fragment 5) was purified. ~75 ng of fragment 4, ~50 ng of fragment 3 and ~50 ng of fragment 5 were combined in a T4 DNA ligase reactin and incubated overnight at 14°, and the reaction mixture transformed into *E. coli* K12 strain 294. Plasmid DNA from six ampicillin resistant transformants were analyzed by restriction endonuclease digestion. One plasmid DNA demonstrated the proper construction and was digested pKCEAInt2.

Final construction was effected by ligating the K-CEA fragment, including the trp promoter from pKCEAInt2 into pBR322(XAP). (pBR322(XAP) is prepared by deletion of the region of pBR322 between its unique AvaI and PvaII sites)

The K-CEA fragment was prepared by treating pKCEAInt2 with Ava I, blunt ending with DNA polymerase I (Klenow fragment) in the presence of DNTPs, digestion with Pst I and isolation of the desired fragment by gel electrophoresis and electroelution.

The large vector fragment from pBR322(XAP) was prepared by successive treatment with EcoR I, blunt ending with polymerase, and redigestion with Pst I, followed by isolation of the large vector fragment by electrophoresis and electroelution.

The K-CEA and large vector fragments as prepared in the preceding paragraphs were ligated with T4 DNA ligase, and the ligation mixture transformed into *E. coli* as above. Plasmid DNA from several ampicillin resistant transformants were selected for analysis, and one plasmid DNA demonstrated the proper construction, and was designated pKCEAtrp207-I*.

E.1.8 Construction of a Plasmid Vector for Direct Expression of Mouse Mature Anti-CEA Heavy (Gamma 1) Chain Gene, pγCEAtrp207-1*

FIG. 7 illustrates the construction of pγCEAtrp207-1*. This plasmid was constructed in two parts beginning with construction of the C-terminal regin of the gamma 1 gene.

5 μg of plasmid pHGH207-1* was digested with Ava I, extended to blunt ends with DNA polymerase I large fragment (Klenow fragment), extracted with phenol/CHCl$_3$, and ethanol precipitated. The DNA was digested with BamH I treated with BAP and the large fragment (fragment A) was purified by 6 percent polyacrylamide gel electrophoresis and electroelution.

~5 μg of pγ11 was digested with Pst I and the gamma chain cDNA insert fragment containing the C-terminal portion of the gene was purified, digested with Ava II followed by extension of the Ava II cohesive ends with Klenow, followed by Taq I digestion. The 375 basepair blunt ended Ava II to Taq I fragment (fragment B) was isolated and purified by gel electrophoresis and electroelution.

9 μg of pγ298 was digested with Taq I and BamH I for isolation of the 496 basepair fragment (fragment C).

Approximately equimolar amounts of fragments A, B, and C were ligated overnight at 14° in 20 μl reaction mixture, then transformed into *E. coli* strain 294. The plasmid DNA from six ampicillin resistant transformants was committed to restriction endonuclease analysis and one plasmid DNA, named pγCEAInt, demonstrated the correct construction of the C-terminal portion of gamma 1 (FIG. 5).

To obtain the N-terminal sequences, 30 μg of pγ298 was digested with Pst I and the 628 basepair DNA fragment encoding the N-terminal region of mouse anti-CEA gamma chain was isolated and purified. This fragment was further digested with Alu I and Rsa I for isolation of the 280 basepair fragment. A 15 nucleotide DNA primer

```
            met  glu  val  met  leu
        5' ATG  GAA  GTG  ATG  CTG 3'
``` was synthesized by the phosphotriester method (supra).

The 5' methionine serves as the initiation codon. 500 ng of this synthetic oligomer primer was phosphorylated at the 5' end in a reaction with 10 units T4 DNA kinase containing 0.5 mM ATP in 20 μl reaction mixture. ~500 ng of the 280 basepair Alu I-Rsa I DNA fragment was mixed with the phosphorylated primer. The mixture was heat denatured for 3 minutes at 95° and quenched in dry-ice ethanol. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C., this primer repair reaction was phenol/CHCl$_3$ extracted, ethanol precipitated, and digested to completion with HpaII. ~50 ng of the expected 125 basepair blund-end to Hpa II DNA fragment (fragment D) was purified from the gel.

A second aliquot of pγ298 DNA was digested with Pst I, the 628 basepair DNA fragment purified by polyacrylamide gel electrophoresis, and further digested with BamH I ahd Hpa II. The resulting 380 basepair fragment (fragment E) was purified by gel electrophoresis.

~5 μg of pγCEAIntI was digested with EcoR I, the cohesive ends were made flush with DNA polymerase I (Klenow), further digested with BamH I, treated with BAP and electrophoresed on a 6 percent polyacrylamide gel. The large vector fragment (fragment F) was isolated and purified.

In a three fragment ligation, 50 ng fragment D, 100 ng fragment E, and 100 ng fragment F were ligated overnight at 4° in a 20 μreaction mixture and used to transform *E. coli* K12 strain 294. The plasmid DNAs from 12 ampicillin resistant transformants were analyzed for the correct construction and the nucleotide sequence surrounding the initiation codon was verified to be correct for the plasmid named pγCEAInt2.

The expression plasmid, pγCEAtrp207-I* used for expression of the heavy chain gene is prepared by a 3-way ligation using the large vector fragment from pBR322(XAP) (supra) and two fragments prepared from pγCEAInt2.

pBR322(XAP) was treated as above by digestion with EcoR1, blunt ending with DNA polymerase (Klenow) in the presence of dNTPs, followed by digestion with Pst I, and isolation of the large vector fragment by gel electrophoresis. A 1543 base pair fragment from pγCEAInt2 containing trp promoter linked with the N-terminal coding region of the heavy chain gene was isolated by treating pγCEAInt2 with Pst I followed by BamH I, and isolation of the desired fragment using PAGE. The 869 base pair fragment containing the C-terminal coding portion of the gene was prepared by partial digestion of pγCEAInt2 with Ava I, blund ending with Klenow, and subsequent digestion with BamH I, followed by purification of the desired fragment by gel electrophoresis.

The aforementioned three fragments were then ligated under standard conditions using T4 DNA ligase, and a ligation mixture used to transform *E. coli* strain 294. Plasmid DNAs from several tetracycline resistant transformants were analyzed; one plasmid DNA demonstrated the proper construction and was designated pγCEAtrp207-1*.

E.1.9. Production of Immunoglobulin Chains by *E. coli*

*E. coli* strain W3110 (ATTC No. 27325) was transformed with pγCEAtrp207-1* or pKCEAtrp207-1* using standard techniques.

To obtain double transformants, *E. coli* strain W3110 cells were transformed with a modified pKCEAtrp207-1*, pKCEAtrp207-1*Δ, which had been modified by cleaving a Pst I-Pvu I fragment from the amp$^R$ gene and religating. Cells transformed with pKCEAtrp207-1*Δ are thus sensitive to ampicillin but still resistant to tetracycline. Successful transformants were retransformed using pγCEAInt2 which confers resistance to ampicillin but not tetracycline. Cells containing both pKCEAtrp207-1*Δ and pγCEAInt2 thus identified by growth in a medium containing both ampicillin and tetracycline.

To confirm the production of heavy and/or light chains in the transformed cells, the cell samples were inoculated into M9 tryptophan free medium containing 10 μg/ml tetracycline, and induced with indoleacrylic acid (IAA) when the OD 550 reads 0.5. The induced cells were grown at 37° C. during various time periods and then spun down, and suspended in TE buffer containing 2 percent SDS and 0.1M β-mercaptoethanol and boiled for 5 minutes. A 10×volume of acetone was added and the cells kept at 22° C. for 10 minutes, then centrifuged at 12,000 rpm. The precipitate was suspended in O'Farrell SDS sample buffer (O'Farrell, P. H., *J. Biol. Chem.*, 250: 4007 (1975)); boiled 3 minutes, recentrifuged, and fractionated using SDS PAGE (10 percent), and stained with silver stain (Goldman, D. et al., *Science* 211: 1437 (1981)); or subjected to Western blot using rabbit anti-mouse IgG (Burnett, W. N., et al., *Anal. Biochem.* 112: 195 (1981)), for identification light chain and heavy chain.

Cells transformed with pγCEAtrp207-1* showed bands upon SDS PAGE corresponding to heavy chain molecular weight as developed by silver stain. Cells transformed with pKCEAtrp207-1* showed the proper molecular weight band for light chain as identified by Western blot; double transformed cells showed bands for both heavy and light chain molecular weight proteins when developed using rabbit anti-mouse IgG by Western blot. These results are shown in FIGS. 8A, 8B, and 8C.

FIG. 8A shows results developed by silver stain from cells transformed with pγCEAtrp207-1*. Lane 1 is monoclonal anti-CEA heavy chain (standard) from CEA.66-E3. Lanes 2b–5b are timed samples 2 hrs, 4 hrs, 6 hrs, and 24 hrs after IAA addition. Lanes 2a–5a are corresponding untransformed controls; Lanes 2c–5c are corresponding uninduced transformants.

Figure 8B:
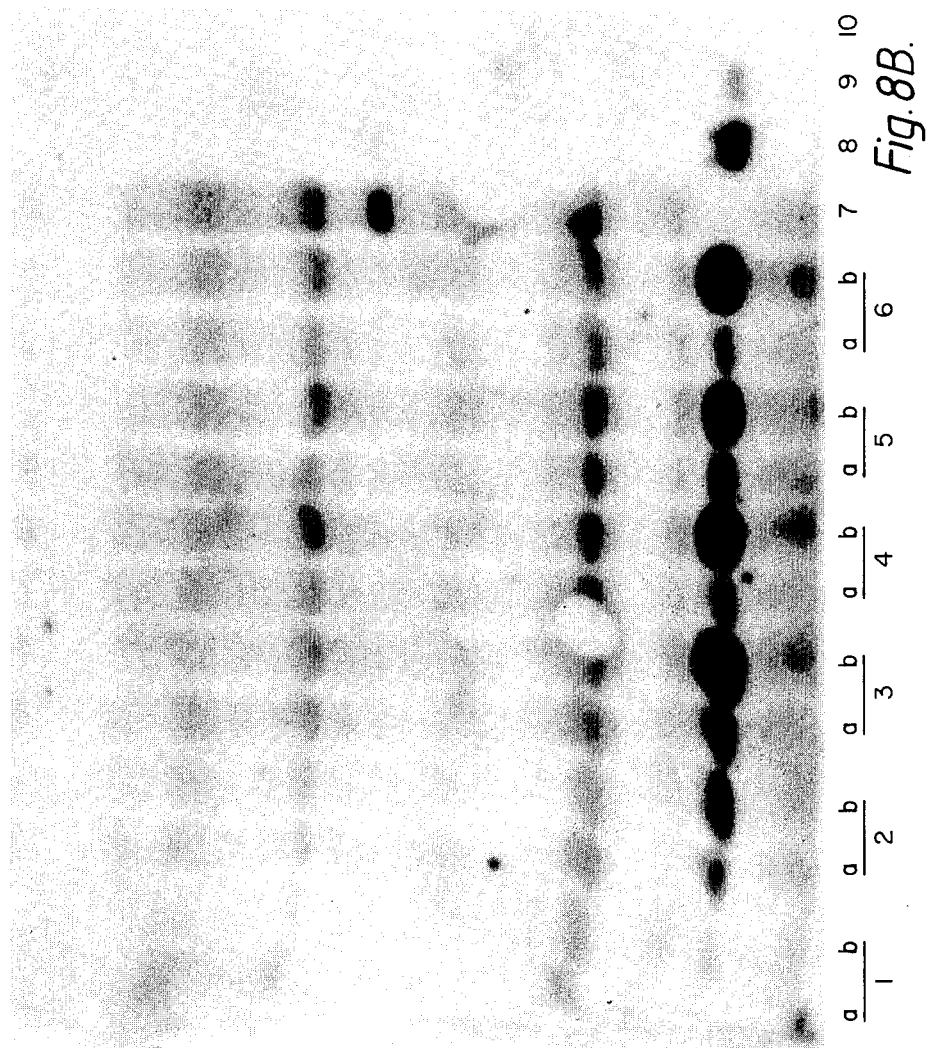

FIG. 8B shows results developed by Western blot from cells transformed with pKCEAtrp207-1*. Lanes 1b–6b are extracts from induced cells immediately, 1 hr, 3.5 hrs, 5 hrs, 8 hrs, and 24 hrs after IAA addition, and 1a–6a corresponding uninduced controls. Lane 7 is an extract from a pγCEAtrp207-1* control, lanes 8, 9, and 10 are varying amounts of anti CEA-kappa chain from CEA.66-E3 cells.

Figure 8C:
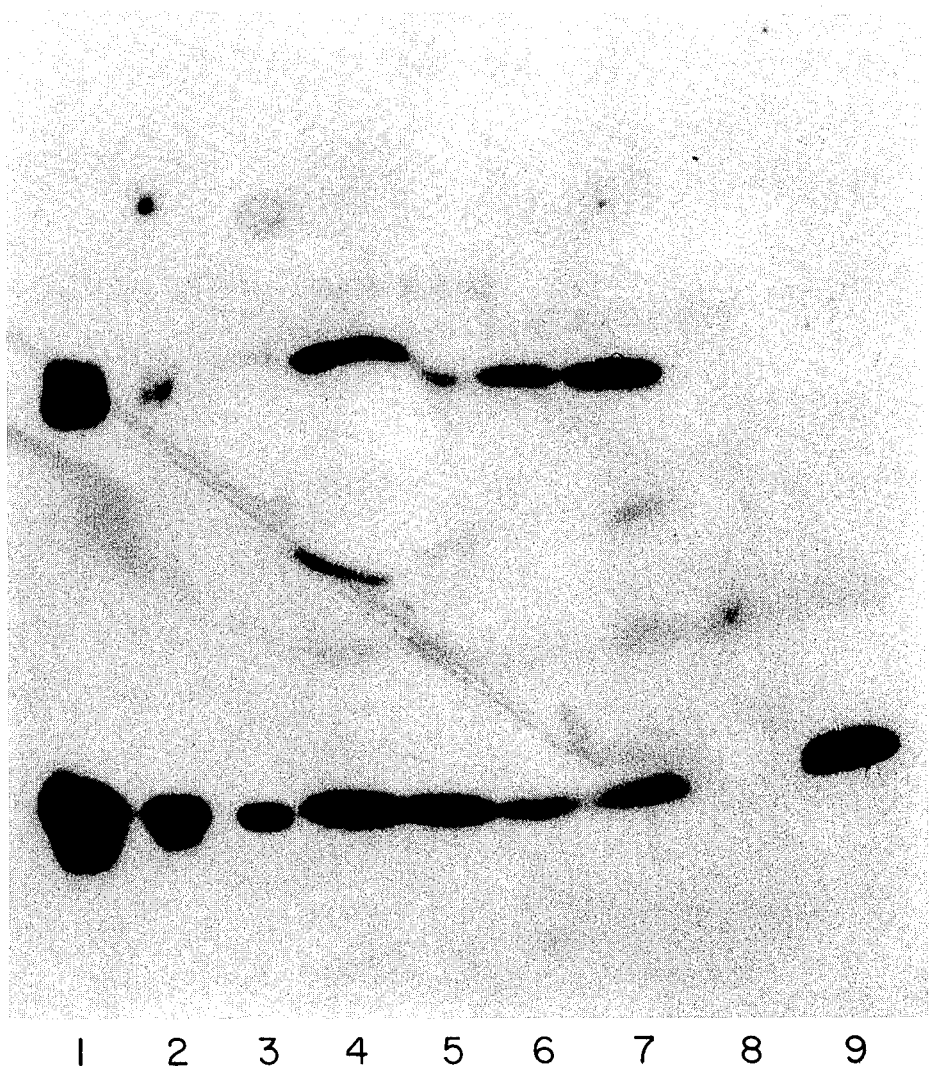

FIG. 8C shows results developed by Western blot from four colonies of double tranformed cells 24 hours after IAA addition (lanes 4–7). Lanes 1–3 are varying amounts of monoclonal gamma chain controls, lanes 8 and 9 are untransformed and pγCEAtrp207-1* transformed cell extracts, respectively.

Figure 9:
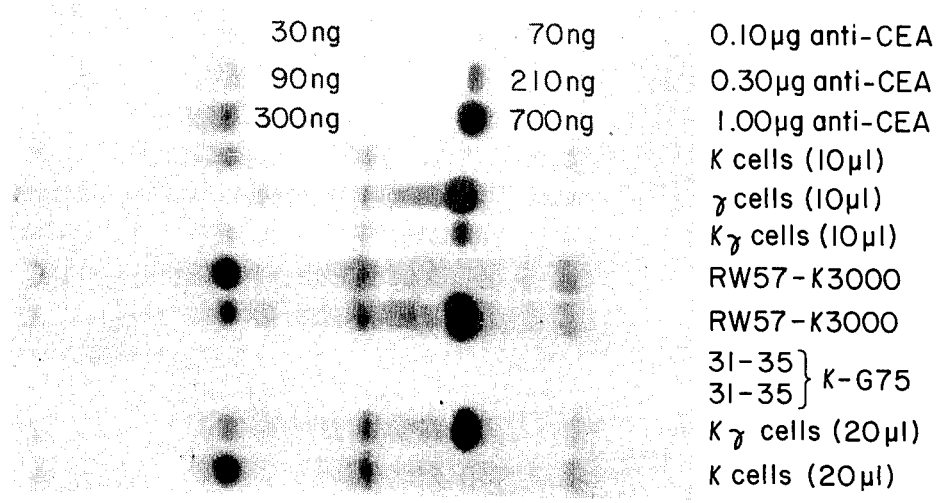
FIG. 9 shows the results of western blots of extracts of cells transformed as those in FIGS. 8.

In another quantitative assay, frozen, transformed E. coli cells grown according to E.1.10 (below) were lysed by heating in sodium dodecyl sulfate (SDS)/β-mercaptoethanol cell lysis buffer at 100°. Aliquots were loaded on an SDS polyacrylamide gel next to lanes loaded with various amounts of hybridoma anti-CEA. The gel was developed by the Western blot, Burnett (supra), using $^{125}$I-labeled sheep anti-mouse IgG antibody from New England Nuclear. The results are shown in FIG. 9. The figure shows that the E. coli products co-migrate with the authentic hybridoma chains, indicating no detectable proteolytic degradation in E. coli. Heavy chain from mammalian cells is expected to be slightly heavier than E. coli material due to glycosylation in the former. Using the hybridoma lanes as a standard, the following estimates of heavy and light chain production were made:

| | (Per gram of cells) |
|---|---|
| E. coli (W3110/pγCEAtrp207-1*) | 5 mg γ |
| E. coli (W3110/pKCEAtrp207-1*) | 1.5 mg K |
| E. coli (W3110/pKCEAtrp207-1*Δ, pγCEA Int2) | 0.5 mg K, 1.0 mg γ |

E.1.10 Reconstitution of Antibody from Recombinant K and Gamma Chains

In order to obtain heavy and light chain preparation for reconstitution, transformed cells were grown in larger batches, harvested and frozen. Conditions of growth of the variously transformed cells were as follows:

E. coli (W3110/pγCEAtrp207-1*) were inoculated into 500 ml LB medium containing 5 μg/ml tetracycline and grown on a rotary shaker for 8 hours. The culture was then transformed to 10 liters of fermentation medium containing yeast nutrients, salts, glucose, and 2 μg/ml tetracycline. Additional glucose was added during growth and at OD 550=20, indoleacrylic (IAA), a trp derepressor, was added to a concentration of 50 μg/ml. The cells were fed additional glucose to a final OD 550=40, achieved approximately 6 hours from the IAA addition.

E. coli (W3110) cells transformed with pKCEA trp 207-1* and double transformed (with pKCEAtrp207-1*Δ and pγCEAInt2) were grown in a manner analogous to that described above except that the OD 550 six hours after IAA addition at harvest was 25–30.

The cells were then harvested by centrifugation, and frozen.

E.2 Assay Method for Reconstituted Antibody

Anti-CEA activity was determined by ELISA as a criterion for successful reconstruction. Wells of microtiter plates (Dynatech Immulon) were saturated with CEA by incubation 100 μl of 2–5 μg CEA/ml solution in 0.1M carbonate buffer, pH 9.3 for 12 hours at room temperature. The wells were then washed 4 times with phosphate buffered saline (PBS), and then saturated with BSA by incubating 200 μl of 0.5 percent BSA in PBS for 2 hours at 37° C., followed by washing 4 times with PBS. Fifty microliters of each sample was applied to each well. A standard curve (shown in FIG. 10), was run, which consisted of 50 μl samples of 10 μg, 5 μg, 1 μg, 500 ng, 100 ng, 50 ng, 10 ng, 5 ng and 1 ng anti-CEA/ml in 0.5 percent BSA in PBS, plus 50 μl of 0.5 percent BSA in PBS alone as a blank. All of the samples were incubated in the plate for 90 minutes at 37° C.

The plates were then washed 4 times with PBS, and sheep anti-mouse IgG-alkaline phosphate (TAGO, Inc.) was applied to each well by adding 100 μl of enzyme concentration of 24 units/ml in 0.5 percent BSA in PBS. The solution was incubated at 37° C. for 90 minutes. The plates wer washed 4 times with PBS before adding the substrate, 100 μl of a 0.4 mg/ml solution of p-nitrophenylphosphate (Sigma) in ethanolamine buffered saline, pH 9.5. The substrate was incubated 90 minutes at 37° C. for color development.

The $A_{450}$ of each well was read by the Microelisa Auto Reader (Dynatech) set to a threshold of 1.5, calibration of 1.0 and the 0.5 percent BSA in PBS (Blank) well set to 0.000. The $A_{450}$ data was tabulated in RS-1 on the VAX system, and the standard curve data fitted to a four-parameter logistic model. The unknown samples' concentrations were calculated based on the $A_{450}$ data.

E.3 Reconstruction of Recombinant Antibody and Assay

Frozen cells prepared as described in paragraph E.1.10 were thawed in cold lysis buffer [10 mM Tris HCl, pH 7.5, 1 mM EDTA, 0.1M NaCl, 1 mM phenylmethylsulfonyl fluoride (PMSF)] and lysed by sonication. The lysate was partially clarified by centrifugation for 20 mins at 3,000 rpm. The supernatant was protected from proteolytic enzymes by an additional 1 mM PmSF, and used immediately or stored frozen at −80° C.; frozen lysates were never thawed more than once.

The S-sulfonate of E. coli produced anti-CEA heavy chain (γ) was prepared as follows: Recombinant E. coli cells transformed with pγCEAtrp207-1* which contained heavy chain as insoluble bodies, were lysed and centrifuged as above; the pellet was resuspended in the same buffer, sonicated and re-centrifuged. This pellet was washed once with buffer, then suspended in 6M guanidine HCl, 0.1M Tris HCl, pH 8, 1 mM EDTA, 20 mg/ml sodium sulfite and 10 mg/ml sodium tetrathionate and allowed to react at 25° for about 16 hrs. The reaction mixture was dialyzed against 8M urea, 0.1M Tris HCl, pH 8, and stored at 4°, to give a 3 mg/ml solution of γ-SSO₃.

650 μl of cell lysate from cells of various E. coli strains producing various IgG chains, was added to 500 mg urea. To this was added β-mercaptoethanol to 20 mM, Tris-HCl, pH 8.5 to 50 mM and EDTA to 1 mM, and in some experiments, γ-SSO₃ was added to 0.1 mg/ml. After standing at 25° for 30–90 mins., the reaction mixtures were dialyzed at 4° against a buffer composed of 0.1M sodium glycinate, pH 10.8, 0.5M urea, 10 mM glycine ethyl ester, 5 mM reduced glutathione, 0.1 mM oxidized glutathione. This buffer was prepared from $N_2$-saturated water and the dialysis was performed in a capped Wheaton bottle. After 16-48 hours, dialysis bags were transferred to 4° phosphate buffered saline containing 1 mM PMSF and dialysis continued another 16-24 hrs. Dialysates were assayed by ELISA as described in paragraph E.2 for ability to bind CEA. The results below show the values obtained by comparison with the standard curve in x ng/ml anti-CEA. Also shown are the reconstitution efficiencies calculated from the ELISA responses, minus the background (108 ng/ml) of cells producing K chain only, and from estimates of the levels of γ and K chains in the reaction mixtures.

|  | ng/ml anti-CEA | Percent recombination |
| --- | --- | --- |
| E. coli W3110 producing IFN-αA (control) | 0 | — |
| E. coli (W3110/pKCEAtrp207-1*) | 108 | — |
| E. coli (W3110/pKCEAtrp207-1*), plus γ-SSO$_3$ | 848 | 0.33 |
| E. coli (W3110/pKCEAtrp207-1*Δ, pγCEA Int2) | 1580 | 0.76 |
| Hybridoma anti-CEA K-SSO$_3$ and γ-SSO$_3$ | 540 | 0.40 |

E.4 Preparation of Chimeric Antibody

FIGS. 11 and 12 show the construction of an expression vector for a chimeric heavy (gamma) chain which comprises the murine anti CEA variable region and human γ-2 constant region.

A DNA sequence encoding the human gamma-2 heavy chain is prepared as follows: the cDNA libary obtained by standard techniques from a human multiple myleoma cell line is probed with 5' GGGCACT-CGACACAA 3' to obtain the plasmid containing the cDNA insert for human gamma-2 chain (Takahashi, et al., *Cell*, 29: 671 (1982), incorporated herein by reference), and analyzed to verify its identity with the known sequence in human gamma-2 (Ellison, J., et al., *Proc. Natl. Acad. Sci. (USA)*, 79: 1984 (1982) incorporated herein by reference).

As shown in FIG. 11, two fragments are obtained from this cloned human gamma 2 plasmid (pγ2). The first fragment is formed by digestion with PvuII followed by digestion with Ava III, and purification of the smaller DNA fragment, which contains a portion of the constant region, using 6 percent PAGE. The second fragment is obtained by digesting the pγ2 with any restriction enzyme which cleaves in the 3' untranslated region of γ2, as deduced fromthe nucleotide sequence, filling in with Klenow and dNTPs, cleaving with Ava III, and isolating the smaller fragment using 6 percent PAGE. (The choice of a two step, two fragment composition to supply the PvuII-3' untranslated fragment provides a cleaner path to product due to the proximity of the AVAIII site to the 3 terminal end thus avoiding additional restriction sites in the gene sequence matching the 3' untranslated region site.) pγCEA207-1* is digested with EcoR 1, treated with Klenow and dNTPs to fill in the cohesive end, and digested with Pvu II, the large vector fragment containing promoter isolated by 6 percent PAGE.

The location and DNA sequence surrounding the PvuII site in the mouse gamma-1 gene are identical to the location and DNA sequence surrounding the PvuII site in the human gamma-2 gene.

The plasmid resulting from a three way ligation of the foregoing fragments, pChim1, contains, under the influence of trp promoter, the variable and part of the constant region of murine anti-CEA gamma 1 chain, and a portion of the gamma 2 human chain. pChim1 will, in fact, express a chimeric heavy chain when tranformed into *E. coli*, but one wherein the change from mouse to human does not take place at the variable to constant junction.

FIG. 12 shows modification of pChim1 to construct pChim2 so that the resulting protein from expression will contain variable region from murine anti CEA antibody and constant region from the human γ-2 chain. First, a fragment is prepared from pChim1 by treating with Nco I, blunt ending with Klenow and dNTPs, cleaving with Pvu II, and isolating the large vector fragment which is almost the complete plasmid except for short segment in the constant coding region for mouse anti CEA. A second fragment is prepared from the previously described pγ2 by treating with Pvu II, followed by treating with any restriction enzyme which cleaves in the variable region, blunt ending with Klenow and dNTPs and isolating the short fragment which comprises the junction between variable and constant regions of this chain.

Ligation of the foregoing two fragments produces an intermediate plasmid which is correct except for an extraneous DNA fragment which contains a small portion of the constant region of the murine anti CEA antigen, and a small portion of the variable region of the human gamma chain. This repair can be made by excising the Xba I to Pvu II fragment and cloning into M13 phage as described by Messing et al., *Nucleic Acids Res.* 9: 309 (1981), followed by in vitro site directed deletion mutagenesis as described by Adelman, et al., DNA, in press (1983) which is incorporated herein by reference. The Xba I-Pvu II fragment thus modified is ligated back into the intermediate plasmid to form pChim2. this plasmid then is capable of expressing in a suitable host a cleanly constructed murine variable/human constant chimeric heavy chain.

In an analogous fashion, but using mRNA templates for cDNA construction for human kappa rather than γ chain, the expression plasmid for chimeric light chain is prepared.

The foregoing two plasmids are then double transformed into *E. coli* W3110, the cells grown and the chains reconstituted as set forth in paragraph E.1–E.3 supra.

E.5 Preparation of Altered Murine Anti-CEA Antibody

E.5.1 Construction of Plasmid Vectors for Direct Expression of Altered Murine Anti-CEA Heavy Chain Gene The cysteine residues, and the resultant disulfide bonds in the region of amino acids 216–230 in the constant region of murine anti-CEA heavy chain are suspected to be imported for complement fixation (Klein, et al., *Proc. Natl. Acad. Sci., (USA)*, 78: 524 (1981)) but not for the antigen binding property of the resulting antibody. To decrease the probability of incorrect disulfide bond formation during reconstruction according to the process of the invention herein, the nucleotides encoding the amino acid residues 226–232 which includes codons for three cysteines, are deleted as follows:

A "deleter" deoxyoligonucelotide, 5' CTAACAC-CATGTCAGGGT is used to delete the relevant portions of the gene from pγCEAtrp207-1* by the procedure of Wallace, et al., *Science,* 209: 1396 (1980). Briefly, the "deleter" deoxyoligonucelotide is annealed with denatured pγCEAtrp207-1* DNA, and primer repair synthesis carried out in vitro, followed by screening by hybridization of presumptive deletion clones with P$^{32}$ labelled deleter sequence.

E.5.2 Production of Cysteine Deficient Altered Antibody

The plasmid prepared in E.5.1 is transformed into an *E.coli* strain previously transformed with pKCEAtrp207-1* as described above. The cells are grown, extracted for recombinant antibody chains, and the altered antibody reconstituted as described in E.1.10.

E.6 Preparation of Fab

E.6.1 Construction of a Plasmid Vector for Direct Expression of Murine Anti-CEA Gamma 1 Fab Fragment Gene pγCEAFabtrp207-1*

FIG. 13 presents the construction of pγCEA-Fabtrp207-1*. 5 μg of pBR322 was digested with Hind III, the cohesive ends made flush by treating with Klenow and dNTPs; digested with Pst I, and treated with BAP. The large vector fragment, fragment I, was recovered using 6 percent PAGE followed by electroelution.

5 μg of pγCEAtrp207-1* was digested with both BamH I and Pst I and the ~1570 bp DNA fragment (fragment II) containing the trp promoter and the gene sequence encoding the variable region continuing into constant region and further into the anti-CEA gamma 1 chain hinge region, was isolated and purified after electrophoresis.

Expression of the anti-CEA gamma 1 chain Fab fragment rather than complete heavy chain requires that a termination condon be constructed at the appropriate location in the gene. For this, the 260 bp Nco I-Nde I DNA fragment from 20 μg of the pγ298 was isolated and purified. A 13 nucleotide DNA primer, the complement of which encodes the last 3 C-terminal amino acids of the Fab gene and 2 bases of the 3 needed for the stop codon, was synthesized by the phosphotriester method (supra). The probe hybridizes to nucleotides 754 to 767 (FIG. 4) which has the following sequence:

Asp Cys Gly Stop
      5' GGGATTGTGGTTG 3'

The third base of the stop codon is provided by the terminal nucleotide of the filled-in Hind III site from pBR322 cleavage described above. 500 ng of this primer was used in a primer repair reaction by phosphorylation at the 5' end in a reaction with 10 units T4 DNA kinase containing 0.5 mM ATP in 20 μl, and mixing with ~200 ng of the Nco I-Nde I DNA fragment. The mixture was heat denatured for 3 minutes at 95° and quenched in dry-ice ethanol. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C., this primer repair reaction was phenol/CHCl$_3$ extracted, ethanol precipitated, digested with BamH I and the reaction electrophoresed through a 6 percent polyacrylamide gel. ~50 ng of the 181 bp blunt end to BamH I DNA fragment, fragment III, was isolated and purified.

~100 ng of fragment I, ~100 ng each of fragments II and III were ligated overnight and transformed into *E. coli* K12 strain 294. Plasmid DNA from several tetracycline resistant transformants was analyzed for the proper construction and the nucleotide sequence through the repair blunt end filled-in Hind III junction was determined for verification of the TGA stop codon.

E.6.2 Production of Fab Protein

The plasmid prepared in E.6.1 is transformed into an *E. coli* strain previously transformed with pKCEAtrp207-1* as described above. The cells are grown, extracted for recombinant antibody chains and the Fab protein reconstituted as described in E.1.10.

We claim:

1. A method comprising
   (a) preparing a DNA sequence encoding a chimeric immunoglobulin heavy or light chain having specificity for a particular known antigen wherein a constant region is homologous to the corresponding constant region of an antibody of a first mammalian species and a variable region thereof is homologous to the variable region of an antibody derived from a second, different mammalian species;
   (b) inserting the sequence into a replicable expression vector operably linked to a suitable promoter compatible with a host cell;
   (c) transforming the host cell with the vector of (b);
   (d) culturing the host cell; and
   (e) recovering the chimeric heavy or light chain from the host cell culture.

2. The method of claim 1 wherein the first mammalian species is human.

3. A composition comprising a chimeric immunoglobulin heavy or light chain having specificity for a particular known antigen having a constant region homologous to a corresponding constant region of an antibody of a first mammalian species and a variable region homologous to a variable region of an antibody derived from a second, different mammalian species.

4. The chimeric heavy or light chain of claim 3 wherein the constant region is human.

5. A replicable expression vector comprising DNA operably linked to a promoter compatible with a suitable host cell, said DNA encoding a chimeric immunoglobulin heavy or light chain having specificity for a particular known antigen and having a constant region homologous to a corresponding region of an antibody of a first mammalian species and a variable region homologous to a variable region of an antibody derived from a second, different mammalian species.

6. The vector of claim 5 wherein the first mammalian species is human.

7. Recombinant host cells transformed with the vector of claim 5.

* * * * *

UNITED STATES PATENT AND TRADEMARK OFFICE
CERTIFICATE OF CORRECTION

PATENT NO. : 4,816,567
DATED : March 28, 1989
INVENTOR(S) : Shmuel Cabilly et al.

It is certified that error appears in the above - identified patent and that said Letters Patent is hereby corrected as shown below:

On the title page, left col. line 10, insert in addition to "Assignee: Genentech, Inc.", --City of Hope, Duarte, Calif.--.
On Col. 5, line 10, change "immunoglobuins" to --immunoglobulins--.
    On Col. 1, line 17, insert --,-- after "proteins".
    On Col. 4, line 9, change "reach" to --reached--.
    On Col. 5, line 14, delete ".".
    On Col. 6, line 28, delete the second "antibodies".
    On col. 6, line 32, change "reference" to --referenced--.
    On Col. 7, line 8, change "respones" to --responses--.
    On Col. 9, line 7, change "$F^{32}$" to --$F^-$--.
    On Col. 10, line 21, change "Examlples" to --Examples--.
    On Col. 16, line 1, change "particular" to --particularly--.
    On Col. 16, line 54, change "formaion" to --formation--.
    On Col. 17, line 38, change "liner" to --linear--.
    On Col. 17, line 62, change "for" to --from--.
    On Col. 18, line 38, change "mous" to --mouse--.
    On Col. 19, line 27, change "from" to --for--.
    On Col. 20, line 57, change "207-1," to --207-1.--.
    On Col. 21, line 6, change "(pH 7.4)" to --(pH 7.4),--.
    On Col. 21, line 21, change "isolted" to --isolated--.
    On Col. 21, line 23, change "precipitaion" to --precipitation--.
    On Col. 21, line 23, change "resuspensionin" to --resuspension in--.
    On Col. 21, line 58, change "sequene" to --sequence--.
    On Col. 22, line 5, change "isoated" to --isolated--.

UNITED STATES PATENT AND TRADEMARK OFFICE
CERTIFICATE OF CORRECTION

Page 2 of 3

PATENT NO. : 4,816,567
DATED : March 28, 1989
INVENTOR(S) : Shmuel Cabilly et al.

It is certified that error appears in the above - identified patent and that said Letters Patent is hereby corrected as shown below:

On Col. 22, line 19, change "reactin" to --reaction--.
On Col. 22, line 25, change "digested" to --designated--.
On Col. 22, line 30, change "PvaII" to --PvuII--.
On Col. 22, line 54, change "regin" to --region--.
On Col. 23, line 44, change "ahd" to --and--.
On Col. 23, line 55, change "µreaction" to --µl reaction--.
On Col. 24, line 9, change "blund" to --blunt--.
On Col. 25, line 16, change "tranformed" to --transformed--.
On Col. 25, line 47, change "preparation" to --preparations--.
On Col. 25, line 55, change "transformed" to --transferred--.
On Col. 26, line 5, change "reconstruction" to --reconstitution--.
On Col. 26, line 7, change "incubation" to --incubating--.
On Col. 26, line 25, change "wer" to --were--.
On Col. 27, line 12, change "reconstruction" to --reconstitution--.
On Col. 27, line 37, change "myleoma" to --myeloma--.
On Col. 27, line 60, change "AVAIII" to --AvaIII--.
On Col. 28, line 64, change "reconstruction" to --reconstitution--.
On Col. 29, line 38, change "condon" to --codon--.
On Col. 30, line 48, change "clain" to --claim--.
On Col. 30, line 55, insert --constant-- between "corresponding" and "region".

UNITED STATES PATENT AND TRADEMARK OFFICE
CERTIFICATE OF CORRECTION

PATENT NO.    : 4,816,567

DATED         : March 28, 1989

INVENTOR(S)   : Shmuel Cabilly, et al.

It is certified that error appears in the above-identified patent and that said Letters Patent is hereby corrected as shown below:

On Col. 21, line 58, change "sequene" to --sequence--.

On Col. 22, line 5, change "isoated" to --isolated--.

Signed and Sealed this

Fourth Day of August, 1992

Attest:

DOUGLAS B. COMER

*Attesting Officer*          Acting Commissioner of Patents and Trademarks